(12) United States Patent
Nakatani et al.

(10) Patent No.: US 9,885,616 B2
(45) Date of Patent: Feb. 6, 2018

(54) THERMAL SHOCK RESISTANCE TESTING METHOD AND THERMAL SHOCK RESISTANCE TESTING APPARATUS

(71) Applicant: NGK Insulators, Ltd., Nagoya (JP)

(72) Inventors: Takahiko Nakatani, Nagoya (JP); Akifumi Kawakami, Nagoya (JP); Masaaki Ito, Nagoya (JP); Yuki Fukumi, Nagoya (JP); Satoshi Sakashita, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 231 days.

(21) Appl. No.: 14/836,072

(22) Filed: Aug. 26, 2015

(65) Prior Publication Data

US 2016/0061758 A1 Mar. 3, 2016

(30) Foreign Application Priority Data

Aug. 28, 2014 (JP) .................. 2014-173594
Jul. 6, 2015 (JP) .................. 2015-135400

(51) Int. Cl.
  *G01N 25/72* (2006.01)
  *G01K 7/02* (2006.01)
  *G01J 5/02* (2006.01)
  *G01N 3/60* (2006.01)

(52) U.S. Cl.
  CPC .................. *G01K 7/02* (2013.01); *G01J 5/02* (2013.01); *G01N 3/60* (2013.01); *G01N 2203/0062* (2013.01)

(58) Field of Classification Search
  None
  See application file for complete search history.

(56) References Cited

U.S. PATENT DOCUMENTS

2004/0026402 A1* 2/2004 Ito ..................... H01L 21/67248
219/444.1

FOREIGN PATENT DOCUMENTS

| CN | 101666733 B | * | 4/2011 |
| JP | 10-170421 A1 | | 6/1998 |
| JP | 10170421 A | * | 6/1998 |
| JP | 2001-083058 A1 | | 3/2001 |

* cited by examiner

*Primary Examiner* — Erica Lin
(74) *Attorney, Agent, or Firm* — Burr & Brown, PLLC (57) ABSTRACT

A ceramic body is heated to a predetermined temperature by using a furnace, and a cooling gas is ejected toward a first end face of the ceramic body so that the first end face of the ceramic body is cooled. At this time, the temperature of the first end face of the ceramic body is measured by a radiation thermometer provided on the same side from which the cooling gas is ejected, and the internal temperature is measured by a thermocouple provided in the ceramic body. Thereafter, a thermal shock resistance test in which actual use conditions are simulated is performed by obtaining the temperature gradient of the ceramic body from measurement results of the temperature of the first end face of the ceramic body and the internal temperature and checking the absence or presence of cracks that occurs to the ceramic body.

9 Claims, 7 Drawing Sheets

THERMAL SHOCK RESISTANCE TESTING METHOD AND THERMAL SHOCK RESISTANCE TESTING APPARATUS

The present application is an application based on JP-2014-173594 filed on Aug. 28, 2014 and JP-2015-135400 filed on Jul. 6, 2015 with Japan Patent Office, the entire contents of which are incorporated herein by reference.

BACKGROUND OF THE INVENTION

Field of the Invention

The present invention relates to a thermal shock resistance testing method of a ceramic body and a thermal shock resistance testing apparatus.

Description of the Related Art

As a catalyst carrier which purifies exhaust gas emitted from an internal combustion engine, a honeycomb structure which is a ceramic body has been widely used. Particularly, for a three-way catalyst carrier for gasoline vehicles is exposed to exhaust gas of high temperature, high thermal shock resistance is necessary. However, the required thermal shock resistance varies depending on the automotive companies, engines, and vehicle types, and thus only a sub-optimized thermal shock resistance testing method has been established.

As a method of evaluating thermal shock resistance, a cold shock testing apparatus has been employed hitherto. In Patent Document 1, a cold and heat shock testing apparatus having a structure in which a testing chamber that accommodates a specimen, a high-temperature chamber, and a low-temperature chamber are separately provided in a state where the testing chamber is interposed, a bumper is installed between the high-temperature chamber and the low-temperature chamber, and hot air and cold air are alternately supplied into the testing chamber is described.

In Patent Document 2, a thermal shock testing apparatus which extracts a test piece that is uniformly heated in a furnace from the furnace, ejects a cooling gas from a side to rapidly cool the test piece and cause an unsteady thermal stress, and measures the temperature of the outer surface of the test piece using a thermographic camera provided on a side opposite to the side where the cooling gas is ejected is described.

[Patent Document 1] JP-A 2001-83058
[Patent Document 2] JP-A 10-170421

SUMMARY OF THE INVENTION

The three-way catalyst carrier for gasoline vehicles needs high thermal shock resistance. However, a method of quantitatively measuring thermal shock resistance for all the automotive companies while simulating actual use conditions has not been established. In addition, in general, cracking occurs to the carriers due to thermal shock generated when the internal temperature of the carrier rapidly drops. However, due to a reduction in the weight of the carrier, it is difficult for a thermocouple to track a rapid change in the internal temperature of the carrier.

In Patent Document 1, the specimen is fixed, and there is a problem in that switching between the hot air and the cold air takes time. In addition, there is a problem of inferior stability and reliability with which the inside of the testing chamber can be accurately maintained at a predetermined temperature. Moreover, since the carrier is cooled from the outside thereof, the actual use conditions cannot be simulated.

In addition, in Patent Document 2, since the entirety of the test piece is extracted from the furnace and the side thereof is cooled, the cooling gas cannot pass through the inside and the actual use conditions cannot be simulated. Furthermore, since the temperature of the outer surface of the test piece is only measured by the thermographic camera, there is a problem in that the internal temperature gradient of the test piece cannot be obtained.

An object of the present invention is to provide a thermal shock resistance testing method of a ceramic body and a thermal shock resistance testing apparatus in which actual use conditions are simulated.

In order to accomplish the object, according to the present invention, a cooling gas is ejected toward a first end face of a ceramic body heated in a furnace so that the first end face of the ceramic body is cooled. At this time, the temperature of the first end face of the ceramic body is measured by a radiation thermometer, and the internal temperature of the ceramic body is measured by a thermocouple provided inside the ceramic body. Thereafter, the temperature gradient of the ceramic body from the measurement results of the temperature of the first end face of the ceramic body and the internal temperature of the ceramic body are obtained, and the absence or presence of cracks that occur to the ceramic body is checked. That is, according to the present invention, a thermal shock resistance testing method and a thermal shock resistance testing apparatus are provided as follows.

[1] A thermal shock resistance testing method including: heating a ceramic body in a furnace to a predetermined temperature; ejecting a cooling gas toward a first end face of the ceramic body heated in the furnace so that the first end face of the ceramic body is cooled; measuring a temperature of the first end face of the ceramic body by using a radiation thermometer provided on the same side from which the cooling gas is ejected, and measuring an internal temperature of the ceramic body by using a thermocouple provided inside the ceramic body; thereafter obtaining a temperature gradient of the ceramic body from measurement results of the temperature of the first end face of the ceramic body and the internal temperature of the ceramic body; checking an absence or presence of a crack that occurs to the ceramic body; and evaluating thermal shock resistance of the ceramic body.

[2] The thermal shock resistance testing method described in [1], in which, after heating the ceramic body in the furnace, moving the first end face of the ceramic body to an open end of the furnace so that the first end face of the ceramic body is cooled.

[3] The thermal shock resistance testing method described in [1] or [2], in which the ceramic body is disposed in the furnace in a state where a protection material is disposed on an outer circumferential surface of the ceramic body.

[4] A thermal shock resistance testing apparatus including: a furnace which heats a ceramic body; a cooling gas ejecting device which ejects a cooling gas for cooling a first end face of the ceramic body from outside of the furnace; a radiation thermometer which measures a surface temperature of the first end face; and a thermocouple which measures an internal temperature of the ceramic body, in which the first end face of the ceramic body is cooled by the cooling gas, the surface temperature of the first end face of the ceramic body is measured by the radiation thermometer, and the internal temperature of the ceramic body is measured by the thermocouple.

[5] The thermal shock resistance testing apparatus described in [4], in which a movement unit which moves the ceramic body in the furnace to dispose the first end face of the ceramic body at an open end of the furnace is provided in the furnace, and the first end face of the ceramic body is disposed at the open end of the furnace so that the first end face of the ceramic body is cooled by the cooling gas.

[6] The thermal shock resistance testing apparatus described in [5], in which a furnace core tube is provided in the furnace, and the movement unit is a pedestal which has a shape that follows a shape of the furnace core tube, and moves in the furnace core tube.

[7] The thermal shock resistance testing apparatus described in [5] or [6], in which the movement unit includes a fixing unit which fixes the thermocouple.

[8] The thermal shock resistance testing apparatus described in any one of [4] to [7], in which a shutter as a shielding portion which shields heat is provided at the open end of the furnace on a side where the first end face of the ceramic body is disposed.

[9] The thermal shock resistance testing apparatus described in any one of [4] to [8], in which the radiation thermometer is installed in a direction at 10° to 60° from a direction perpendicular to the first end face of the ceramic body.

In the thermal shock resistance testing method and the thermal shock resistance testing apparatus of the present invention, the cooling gas is ejected toward and cools the first end face of the ceramic body heated in the furnace, and thus a rapid temperature change can be generated.

In addition, the temperature of the first end face of the ceramic body is measured by the radiation thermometer, the internal temperature of the ceramic body is measured by the thermocouple provided in the ceramic body, the temperature gradient of the ceramic body is thereafter obtained from the measurement results of the temperature of the first end face of the ceramic body and the internal temperature of the ceramic body, and the absence or presence of cracks that occur to the ceramic body is checked. Accordingly, the thermal shock resistance of the ceramic body can be quantitatively measured.

DESCRIPTION OF THE PREFERRED EMBODIMENTS

Hereinafter, embodiments of the present invention will be described with reference to the drawings. The present invention is not limited to the following embodiments, and changes, modifications, and improvement can be made without departing from the scope of the present invention.

Figure 1:
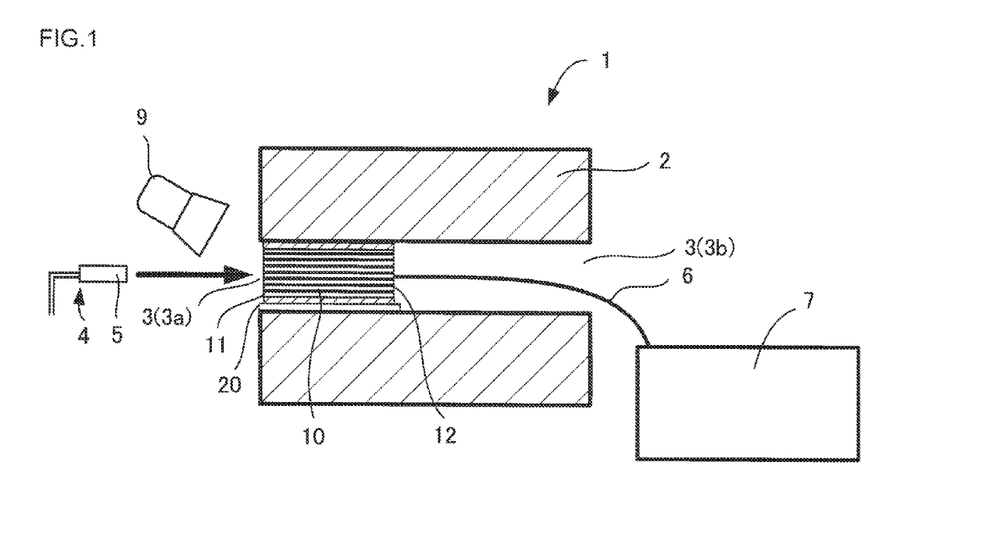
FIG. 1 is a sectional view of a thermal shock resistance testing apparatus.

FIG. 1 shows a sectional view of a thermal shock resistance testing apparatus 1 of the present invention. The thermal shock resistance testing apparatus 1 includes a furnace 2 which heats a ceramic body 10, a cooling gas ejecting device 4 which ejects a cooling gas, a radiation thermometer 9 which measures a surface temperature, and a thermocouple 6. The cooling gas ejecting device 4 ejects the cooling gas for cooling a first end face 11 of the ceramic body 10 from the outside of the furnace 2 in a state where the ceramic body 10 remains in the furnace 2. The radiation thermometer 9 is used to measure the surface temperature of the first end face 11 of the ceramic body 10, and the thermocouple 6 is used to measure the internal temperature of the ceramic body 10. The thermal shock resistance testing apparatus 1 heats the ceramic body 10, cools the first end face 11 of the ceramic body 10 using the cooling gas, measures the surface temperature of the first end face 11 using the radiation thermometer 9, and measures the internal temperature of the ceramic body 10 using the thermocouple 6.

Figure 5:
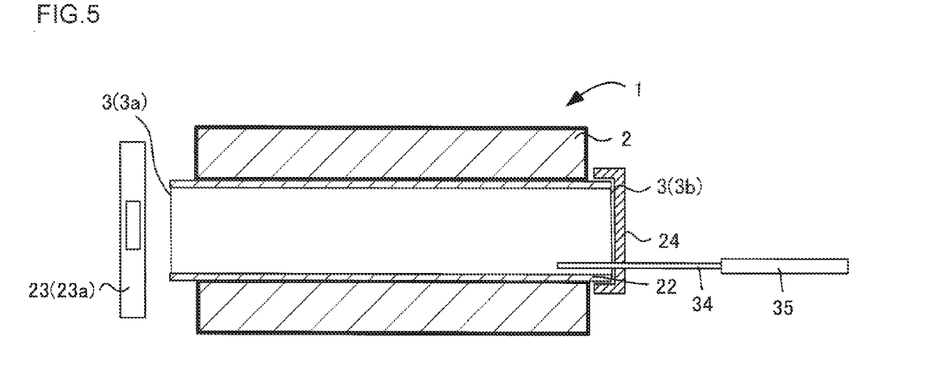
FIG. 5 is a sectional view showing a state where open ends of the furnace is covered with a shielding portion and a cover.
Figure 9A:
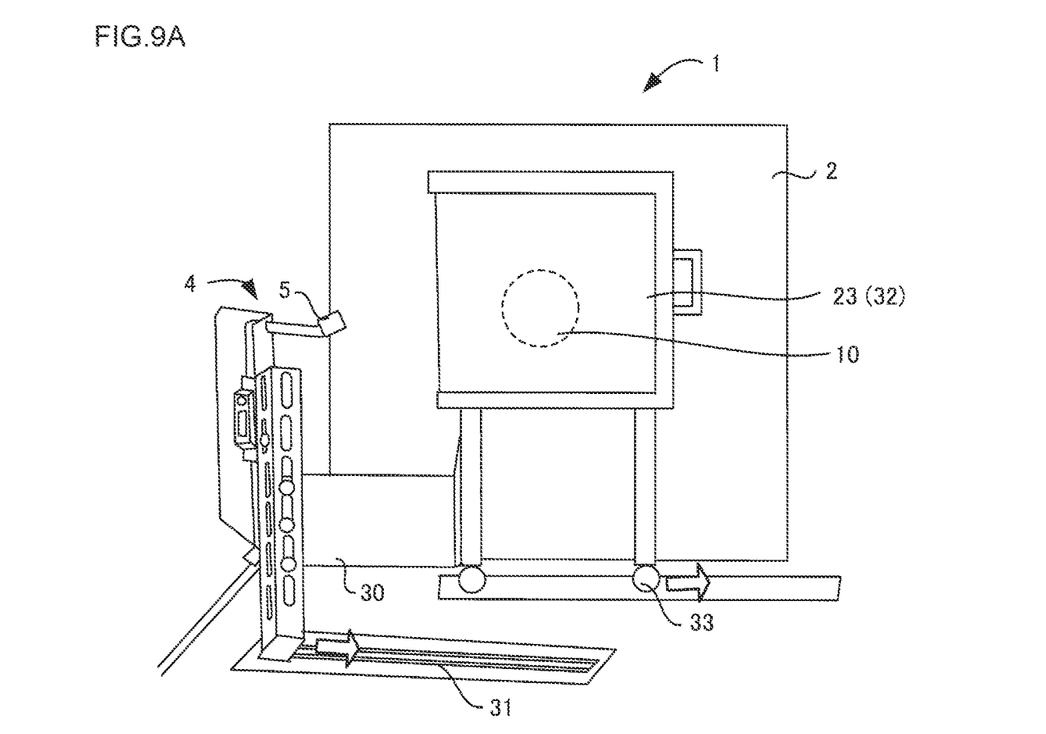
FIG. 9A is an explanatory view showing a sliding mechanism.

The furnace 2 includes an open end 3 at at least one end thereof, through which the ceramic body 10 is moved in or out. In addition, as shown in FIG. 5, the open end 3 may be provided with a shielding portion 23 to prevent leakage of internal heat when the ceramic body 10 is heated. As the shielding portion 23, a door that can be opened and closed, a cover 23a having a shape that covers the open end 3, or a shutter 32 may be employed. As shown in FIG. 9A, it is particularly preferable that the shutter 32 is provided over the open end 3 (first open end 3a) of the furnace 2 on a side where the first end face 11 of the ceramic body 10 is disposed (on a side provided with the radiation thermometer 9 and the cooling gas ejecting device 4). Since the shielding portion 23 having a shape like the shutter 32 is provided on the first open end 3a of the furnace 2, after the first end face 11 of the ceramic body 10 is moved to the first open end 3a of the furnace 2, the shielding portion 23 is opened and then the ejection of the cooling gas and the temperature measurement can be instantly performed.

It is preferable that the size of the open end 3 of the furnace 2 is greater than the diameter of the ceramic body 10 by +5% to 25%. By allowing the clearance between the open end 3 and the ceramic body 10 to be in the above numerical range, the movement of the ceramic body 10 is facilitated, and heat from the furnace 2 can be efficiently used to increase the temperature of the ceramic body 10. With such open end 3, only the first end face 11 of the ceramic body 10 is exposed to the outside.

Figure 2:
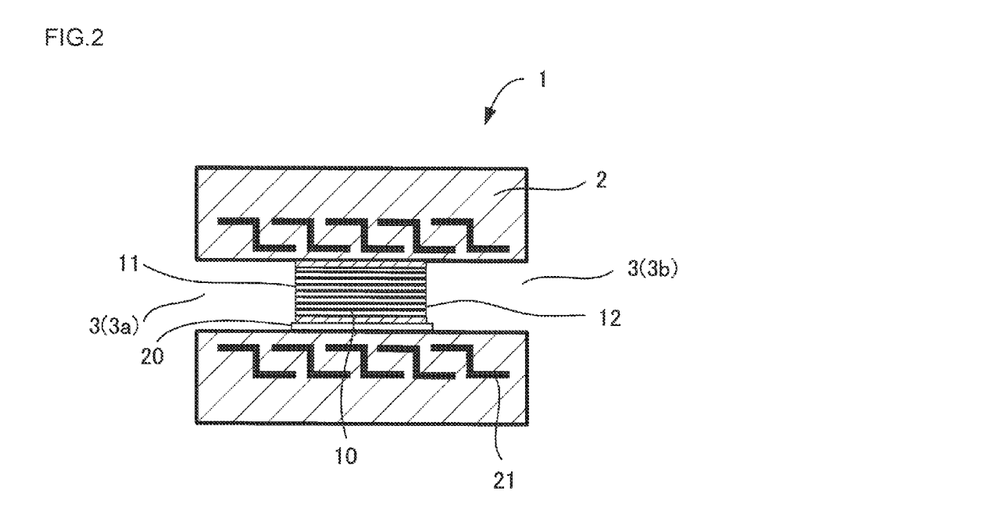
FIG. 2 is a sectional view showing a state where a ceramic body is heated.

The furnace 2 preferably has a tube shape and is preferably configured to heat the ceramic body 10 in the tube. As shown in FIG. 5, the furnace 2 may include a furnace core tube 22. Furthermore, as shown in FIG. 2, the furnace 2 is preferably configured such that a heater 21 is disposed inside a refractory material to heat the inside of the tube of the furnace 2. The ceramic body 10 is heated by the furnace 2 and is thus uniformly heated. However, the internal shape of the tubular furnace 2 is not limited to a circular shape. The external shape of the furnace 2 is not limited to a circular shape. Furthermore, on a side opposite to the first open end 3a of the furnace 2 in the longitudinal direction thereof, a second open end 3b is preferably provided.

Figure 6:
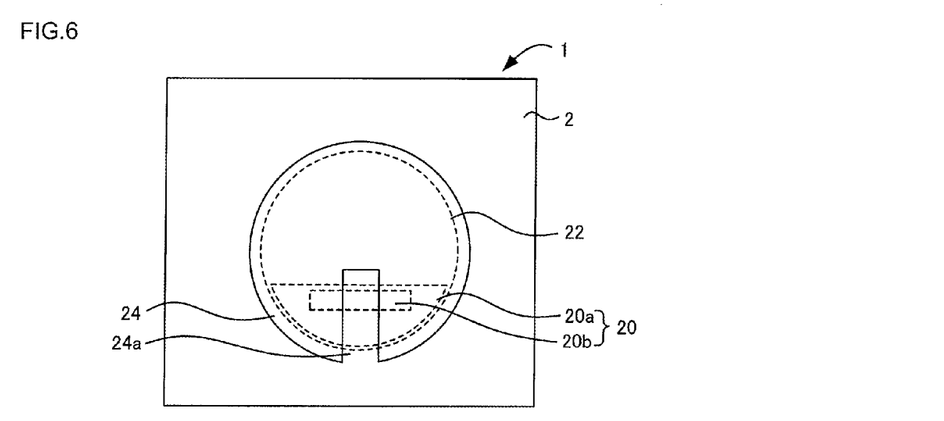
FIG. 6 is an explanatory view showing the cover that covers the second open end of the furnace.

As shown in FIG. 5, the second open end 3b of the furnace 2 is preferably provided with a cover 24. By providing the cover 24, the internal temperature of the furnace 2 can be maintained. As shown in FIG. 6, the cover 24 preferably has the same shape as the external shape of the second open end 3b of the furnace core tube 22.

Figure 3:
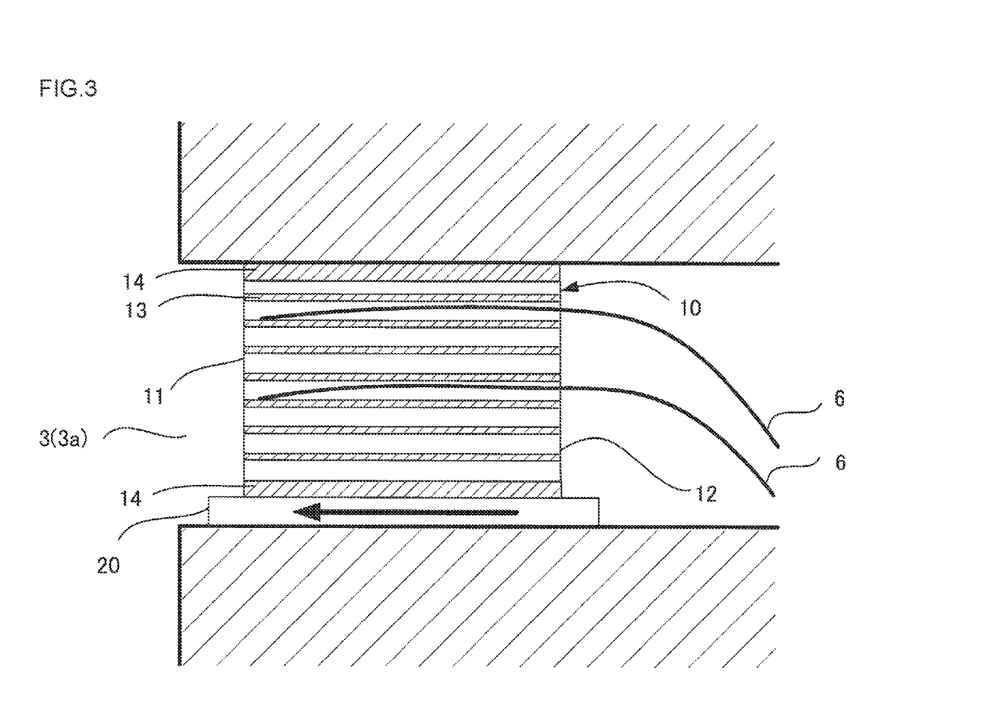
FIG. 3 is a sectional view showing a state where a first end face of the ceramic body is moved to a first open end of the furnace.

In addition, as shown in FIG. 3, in the thermal shock resistance testing apparatus 1 of the present invention, a movement unit 20 which moves the ceramic body 10 in the furnace 2 to dispose the first end face 11 at the first open end 3a may be provided in the furnace 2. The movement unit 20 may be a pedestal 20a which can be pushed by a heat-resistant bar 34 or the like from the second open end 3b of the furnace 2.

Figure 7:
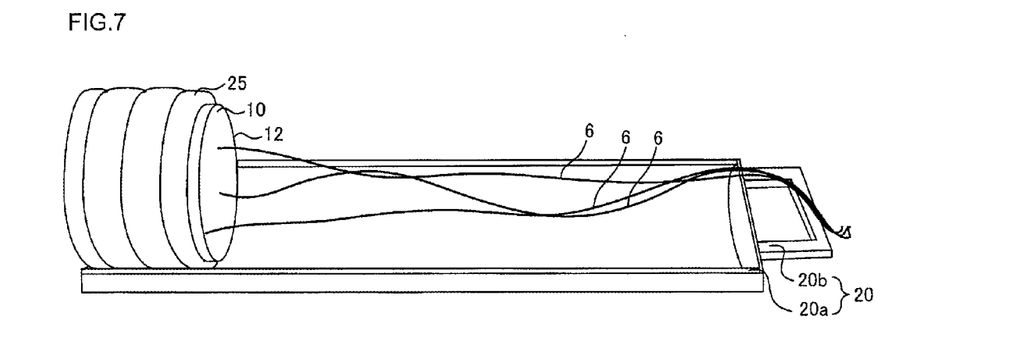
FIG. 7 is an explanatory view showing a state where the ceramic body is disposed on a movement unit.
Figure 8A:
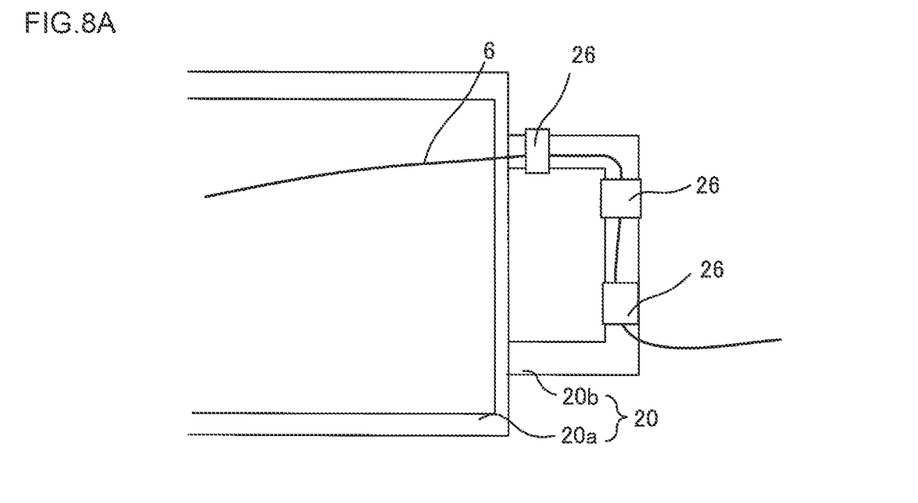
FIG. 8A is an explanatory view showing a state of a handle provided to the movement unit, when viewed from above.
Figure 8B:
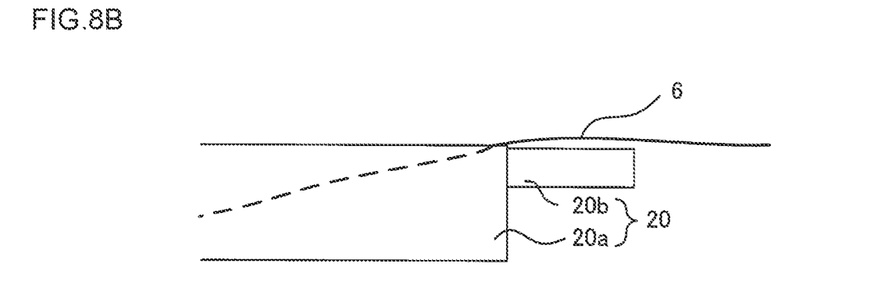
FIG. 8B is an explanatory view showing a state of the handle provided to the movement unit, when viewed from a side.

As shown in FIG. 7, the movement unit 20 preferably includes the pedestal 20a having a shape that follows the shape of the furnace core tube 22 of the furnace 2. That is, a surface of the pedestal 20a that comes into contact with the furnace core tube 22, i.e., the bottom surface is preferably curved along the furnace core tube 22 when the furnace core tube 22 is curved. Since the pedestal 20a has the shape that follows the shape of the furnace core tube 22, the ceramic body 10 can be easily moved. Furthermore, as shown in FIGS. 7, 8A, and 8B, the pedestal 20a is preferably provided with a handle 20b for fixing the heat-resistant bar 34 to move the pedestal 20a forward and rearward using the heat-resistant bar 34.

In order to move the first end face 11 of the ceramic body 10 to the first open end 3a of the furnace 2 without decreasing the internal temperature of the furnace 2, the cover 24 provided at the second open end 3b preferably has a penetration portion formed therein. As the penetration portion, a slit 24a or a hole may be employed. As shown in FIG. 6, since the slit 24a is provided in the cover 24, the pedestal 20a on which the ceramic body 10 is placed can be pushed by inserting the heat-resistant bar 34 from the slit 24a. Since the operation can be performed in a state where the second open end 3b is covered with the cover 24, the first end face 11 of the ceramic body 10 can be moved to the first open end 3a of the furnace 2 without decreasing the internal temperature of the furnace 2. In addition, in order to push the pedestal 20a, an air cylinder 35 is preferably used. Since the air cylinder 35 has a function of arbitrarily controlling speed, the pedestal 20a can be pushed and moved at a constant speed with high reproducibility by the bar 34 provided with the air cylinder 35.

Furthermore, it is preferable that the movement unit 20 described above includes fixing means to fix the thermocouple 6. It is preferable that fasteners 26 or the like are used on the pushing side of the movement unit 20 as the fixing means to fix the thermocouple 6. More preferably, the thermocouple 6 is fixed in an L-shape onto the handle 20b provided in the pedestal 20a as shown in FIG. 8A. By fixing the thermocouple 6 to the movement unit 20, deviation that occurs when the thermocouple 6 is pulled during movement can be prevented.

In addition, the cooling gas ejecting device 4 that cools the first end face 11 of the ceramic body 10 is provided outside the furnace 2. The cooling gas ejecting device 4 includes a cooling gas ejecting nozzle 5 provided in a state of corresponding to the position of the first end face 11 of the ceramic body 10 disposed at the open end 3 of the furnace 2. Here, a rectilinear ejection type nozzle is used in the cooling gas ejecting device 4. In order to prevent the cooling gas ejecting device 4 from being heated by radiant heat from the furnace 2, as shown in FIG. 9A, a sliding mechanism is preferably provided which disposes the cooling gas ejecting device 4 in a place distant from the furnace 2 until the start of cooling and instantly moves the cooling gas ejecting device 4 to a cooling start position for cooling.

As shown in FIG. 9A, the sliding mechanism is configured so that the cooling gas ejecting device 4 and the shutter 32 which is the shielding portion 23 that covers the first open end 3a of the furnace 2 are connected to each other by a cooling device shutter connection arm 30 to allow the cooling gas ejecting device 4 and the shutter 32 simultaneously slide. A rail 31 is provided in the lower portion of the cooling gas ejecting device 4 and the cooling gas ejecting device 4 slides on the rail 31. The cooling gas ejecting nozzle 5 is moved to the cooling start position which is a position that faces the first end face 11 of the ceramic body 10. Since a caster 33 is provided in the lower portion of the shutter 32, as the cooling gas ejecting device 4 is moved, the shutter 32 that covers the open end 3 of the furnace 2 is moved to become distant from the open end 3. Accordingly, cooling can be started as soon as the cooling gas ejecting nozzle 5 is moved to the cooling start position. In addition, since the shutter 32 covers the open end 3 of the furnace 2 until immediately before the start of the cooling, a change in the internal temperature of the furnace 2 due to the open end of the shutter 32 can be reduced.

In the embodiment shown in FIG. 9A, the cooling gas ejecting device 4 and the shutter 32 which is the shielding portion 23 are connected to each other by the cooling device shutter connection arm 30. However, they may not be connected to each other and may be configured to be individually controlled in an electrical or mechanical manner and independently moved.

Figure 9B:
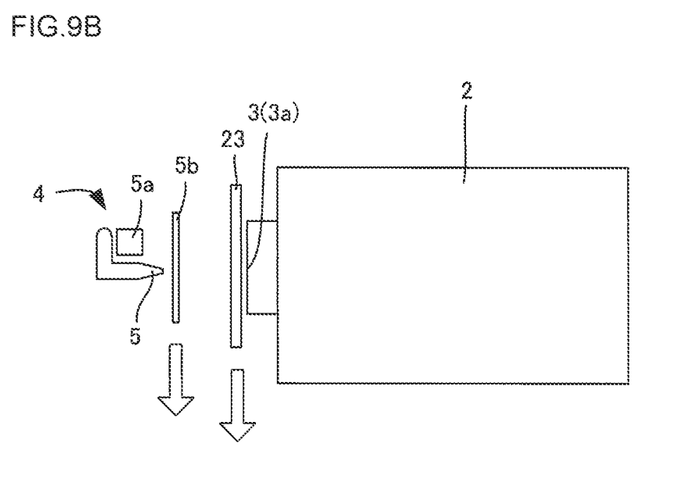
FIG. 9B is a view showing an embodiment in which a heat shielding portion for preventing heating of a cooling gas ejecting device is provided.

FIG. 9B is a view of the vicinity of the open end 3 (first open end 3a) of the furnace 2 viewed from above, and shows an embodiment in which a heat shielding portion 5b is provided. As shown in FIG. 9B, in this embodiment in order to prevent the cooling gas ejecting device 4 from being heated by radiant heat from the furnace 2, the heat shielding portion 5b (for example, a heat shielding plate formed of a plate having insulating properties) is installed between the cooling gas ejecting device 4 and the furnace 2. The cooling gas ejecting nozzle 5 of the cooling gas ejecting device 4 is supported by a support bar 5a, and between the cooling gas ejecting nozzle 5 and the open end 3 of the furnace 2, the shielding portion 23 (the shutter 32) is provided on the open end 3 side, and the heat shielding portion 5b is provided on the cooling gas ejecting nozzle 5 side.

In this case, the heat shielding portion 5b may be provided with a sliding mechanism capable of moving the heat shielding portion 5b at the time of the start of cooling. In a case where the heat shielding portion 5b is provided, the cooling gas ejecting device 4 may be provided to oppose the open end 3 of the furnace 2 so that the cooling gas ejecting device 4 is not moved. Otherwise, the cooling gas ejecting device 4 may also be configured to be disposed to oppose the open end 3 of the furnace 2 at the time of heating the ceramic body 10. The shielding portion 23 (the shutter 32) and the heat shielding portion 5b may be controlled while being interlocked with each other. In this case, at the time of the start of cooling, the shielding portion 23 (the shutter 32) may be configured to slide to be opened and at the same time, the heat shielding portion 5b may be configured to slide to be opened. After the shielding portion 23 (the shutter 32) and the heat shielding portion 5b are allowed to be opened, the cooling gas is ejected from the cooling gas ejecting nozzle 5 disposed in advance to oppose the open end 3 of the furnace 2.

Figure 10:
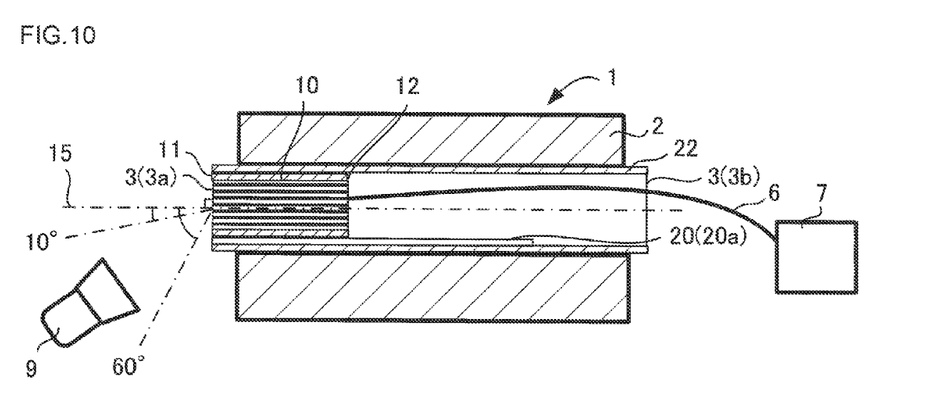
FIG. 10 is an explanatory view showing an angle at which a radiation thermometer is provided.

In addition, the radiation thermometer 9 which measures the temperature of the first end face 11 of the ceramic body 10 is provided outside the furnace 2. Accordingly, the thermal distribution state at the first end face 11 of the ceramic body 10 can be detected in real-time. As shown in FIG. 10, it is preferable that the radiation thermometer 9 is installed in a direction at 10° to 60° from a direction (center axis 15) perpendicular to the first end face 11 of the ceramic body 10. In a case where the installation direction is at an angle of lower than 10°, noise transmitted through the through holes of the ceramic body 10 is likely to affect the measurement. On the other hand, in a case where the installation direction is at an angle of higher than 60°, infrared light from the ceramic body 10 may not be accurately measured. Therefore, by allowing the installation direction to be a direction at an angle of 10° to 60° from the direction perpendicular to the first end face 11 of the ceramic body 10, the surface temperature of the first end face 11 of the ceramic body 10 can be accurately measured. In addition, in order to prevent a lens to be broken by radiant heat, the installation position of the radiation thermometer 9 is preferably located at a distance at which the temperature of the body of the radiation thermometer 9 from the first end face 11 of the ceramic body 10 is 50° C. or lower.

As the radiation thermometer 9, a detection device which detects infrared rays emitted from the ceramic body 10 can be appropriately used. As the detection device which detects infrared rays, an infrared radiation camera, an infrared radiation thermometer, or the like may be employed. By measuring the surface image of the first end face 11 of the ceramic body 10 using the infrared radiation camera, the temperature distribution of the first end face 11 can be measured as a thermal image. The thermal image is sent to a thermal image display device to be displayed as an image such that the temperature distribution of the first end face 11 can be checked as the thermal image.

In addition, the thermocouple 6 is provided in the ceramic body 10 to measure and track the internal temperature of the ceramic body 10. As shown in FIG. 3, one or more thermocouples 6 may be provided in the ceramic body 10. By providing a plurality of thermocouples 6, the temperatures of a plurality of points in the ceramic body 10 can be tracked. In addition, it is preferable that the thermocouple 6 is inserted from a second end face 12 side which is a side opposite to the first end face 11 of the ceramic body 10 for installation. Since the thermocouple 6 is provided on the second end face 12 side, direct contact between the thermocouple 6 and the cooling gas can be prevented. As described above, when the thermocouple 6 is provided on the second end face 12 side of the ceramic body 10, it is preferable that the thermocouple 6 is inserted from the second open end 3b side of the furnace 2. As the thermocouple 6 is inserted from the second open end 3b side of the furnace 2, direct contact between the thermocouple 6 and the cooling gas can further be prevented. In addition, in order to accurately measure at a desired measurement position, it is preferable that the length of the thermocouple 6 is set to a length to which the rate of expansion calculated from the thermal expansion coefficient during heating is applied. In addition, the thermocouple 6 is connected to a data logger 7 for recording temperatures via a wire. The data logger 7 is provided outside the furnace 2.

As the ceramic body 10, for example, a honeycomb structure may be employed. In the honeycomb structure, a honeycomb structure body formed by porous partition walls 13 and a circumferential wall 14 positioned in the outermost circumference are provided. In the honeycomb structure, a plurality of cells which penetrate from the first end face 11 (inflow end face) which is one end face to the second end face 12 (outflow end face) which is the other end face and which form flow passages for a fluid are defined by the partition walls 13 (see FIGS. 4A and 4B).

It is preferable that the partition walls 13 and the circumferential wall 14 of honeycomb structures contain ceramics as the primary components. Among the ceramics, cordierite, silicon carbide, a silicon-silicon carbide composite material, mullite, alumina, aluminum titanate, silicon nitride, or a silicon carbide-cordierite composite material may be employed. When the "primary component" is mentioned in the specification, it means that 50 mass % or higher of the component is contained with respect to the total content.

As the honeycomb structure used in the thermal shock resistance test, for example, a catalyst carrier on which a catalyst is loaded on the partition walls 13 or in the pores of the partition walls 13 and is used to purify exhaust gas emitted from an internal combustion engine or the like may be employed. As the catalyst, a three-way catalyst for purifying gasoline vehicle exhaust gases may be employed, and the honeycomb structure may also be a three-way catalyst carrier for gasoline vehicles. The three-way catalyst is a catalyst which mainly purifies hydrocarbons (HC), carbon monoxide (CO), and nitrogen oxides (NOx). As the three-way catalyst, for example, a catalyst containing platinum (Pt), palladium (Pd), or rhodium (Rh) may be employed. It is to be noted that, the catalyst carrier which is the ceramic body 10 may also load an SCR catalyst, a NOx storage catalyst, or an oxidation catalyst, and the object of the thermal shock resistance test is not limited thereto.

The overall shape of the honeycomb structure is a round-pillar shape (cylindrical shape), and the shape of the cells (the shape of a cross-section cut in the radial direction of the honeycomb structure in a plane perpendicular to the communication direction of the cells) is not limited to a quadrangular shape. For example, the overall shape thereof may also be an elliptical pillar shape, an oblong pillar shape, a quadrangular pillar shape, a triangular pillar shape, or other polygonal pillar shapes. The shape of the cells of the honeycomb structure may also be a hexagonal shape, a triangular shape, or the like. The open ends 3 at the end face of predetermined cells in the honeycomb structure may also be plugged.

Hereinafter, the thermal shock resistance testing method of the present invention will be described. In the thermal shock resistance testing method of the present invention, first, the ceramic body 10 is heated in the furnace 2 to a predetermined temperature. Next, the cooling gas is ejected toward the first end face 11 of the ceramic body 10 so as to be cooled. At this time, the temperature of the first end face 11 of the ceramic body 10 is measured by the radiation thermometer 9 provided on the same side as the side where the cooling gas is ejected, and the internal temperature of the ceramic body 10 is measured by the thermocouple 6 provided in the ceramic body 10. Thereafter, the thermal shock resistance of the ceramic body 10 is evaluated by obtaining, from the measurement results of the temperature of the first end face 11 of the ceramic body 10 and the internal temperature of the ceramic body 10, the temperature gradient of the ceramic body 10, and checking the absence or presence of cracks that occur to the ceramic body 10. As the ceramic body 10 which is the object of the thermal shock resistance test, the above-described honeycomb structure may be employed. However, the object is not limited thereto.

As shown in FIG. 7, it is preferable that the ceramic body 10 is disposed in the furnace 2 in a state where a protection material is disposed on the outer circumferential surface of the ceramic body 10. The protection material preferably has elasticity and a thickness, and for example, a mat 25 is employed. By winding the mat 25 around the outer circumferential surface of the ceramic body 10, not only the ceramic body 10 can be protected, but also cooling of the ceramic body 10 from the outer circumferential portion thereof during the test can be reduced. In addition, as shown in FIG. 2, it is preferable that heating of the ceramic body 10 is performed at the center portion of the furnace 2. When heating is performed at the center portion of the furnace 2, the ceramic body 10 can be uniformly heated. Regarding the heating temperature, the heating is preferably performed at 900° C. or higher as in heating by exhaust gas of an actual vehicle.

In addition, regarding the ceramic body 10, after the ceramic body 10 is heated in the furnace 2, the first end face 11 of the ceramic body 10 may be moved to the first open end 3a of the furnace 2 to cool the first end face 11 of the ceramic body 10. After the ceramic body 10 is heated in the furnace 2, for example, at a predetermined test temperature of 900° C. to 1100° C., for example, for 5 minutes to 30 minutes, as shown in FIG. 3, in a state where the ceramic body 10 is placed on the movable pedestal, the first end face 11 of the ceramic body 10 is moved to the first open end 3a of the furnace 2 so as to be disposed at the first open end 3a.

Disposing the first end face 11 of the ceramic body 10 at the first open end 3a of the furnace 2 means disposing the first end face 11 to be aligned with the edge of the first open end 3a of the furnace 2 in a state where the ceramic body 10 remains in the furnace 2. However, as long as the first end face 11 is hit by the cooling gas when the cooling gas is ejected and the temperature of the first end face 11 can be measured by the radiation thermometer 9, the first end face 11 of the ceramic body 10 may not be disposed to be aligned with the edge of the first open end 3a of the furnace 2 but may be disposed in the furnace 2 or in the vicinity of the first open end 3a of the furnace 2.

As described above, after the first end face 11 of the ceramic body 10 is disposed at the first open end 3a of the furnace 2 and heated, the cooling gas ejecting nozzle 5 of the cooling gas ejecting device 4 is instantly allowed to approach the first end face 11 and ejects the cooling gas. The cooling gas preferably has a temperature of 200° C. or lower as is actually used during cooling of a three-way catalyst carrier for a vehicle. By ejecting the cooling gas as described above, a state where a low-temperature gas suddenly flows into the ceramic body 10 at a high temperature can be reproduced, and a rapid temperature change can be generated. In addition, by controlling the temperature and flow rate of the cooling gas, the rapid temperature change in the ceramic body 10 can be controlled.

Regarding the rapidly cooled state of the first end face 11 of the ceramic body 10, the temperature of the outer surface of the first end face 11 is measured in real-time by the radiation thermometer 9 provided on the same side as the side where the cooling gas is ejected. Simultaneously with this, the internal temperature of the ceramic body 10 is tracked by the thermocouple 6 provided inside the ceramic body 10. In addition, the cooling gas ejecting device 4, the radiation thermometer 9, and the data logger 7 may be configured to be connected to each other so that data is acquired by the radiation thermometer 9 with a time axis of the data logger 7 for temperature recording using the ejection of the cooling gas by the cooling gas ejecting device 4 as a trigger. When such a trigger function is provided, a change in the temperature of the outer surface of the first end face 11 after the ejection of the cooling gas and a change in the internal temperature of the ceramic body 10 can be recorded in association with time.

Thereafter, from the measurement results of the temperature of the first end face 11 of the ceramic body 10 and the internal temperature of the ceramic body 10, the actual temperature gradient of the ceramic body 10 is obtained through a simulation. Since the thermocouple 6 itself has its own heat capacity, a rapid temperature change cannot be tracked. With the temperature measurement results of the thermocouple 6 only, the measured temperatures are lower than the actual internal temperatures. Therefore, by using the simulation, the temperature gradient of the actual internal temperature can be obtained, and thus actual use conditions can be simulated. This simulation is subjected in advance to matching to measurement results in a case where a temperature change that can be tracked by the thermocouple 6 is given.

After measuring the temperatures, the absence or presence of cracks in the ceramic body 10 is checked visually or by using a microscope. By performing measurement as described above, the thermal shock resistance of the ceramic body 10 can be quantitatively measured.

EXAMPLES

Hereinafter, the present invention will be described in detail on the basis of Examples, and the present invention is not limited to Examples.

(Sample 1 and Sample 2)

As ceramic bodies 10 of Sample 1 and Sample 2, ceramic honeycomb structures having a diameter of 100 mm and a longitudinal length of 100 mm were produced. The wall thickness of Sample 1 was 90 µm. The wall thickness of Sample 2 was 64 µm.

Example 1

Sample 1 was heated in a tubular electric furnace 2 having an inner diameter of 110 mm and a longitudinal length of 1500 mm at 1000° C. for 60 to 120 minutes. Thereafter, the first end face 11 of the honeycomb structure was moved to the first open end 3a of the furnace 2 and a cooling gas at room temperature was ejected thereto to cool the first end face 11 for 2 minutes to 5 minutes (in Example 1, a heating and cooling cycle was not present unlike in Comparative Example 1). At this time, by changing the flow rate of the cooling gas in a range of 10 to 200 L/min, temperature differences that had occurred to the honeycomb structure were controlled.

Figure 4A:
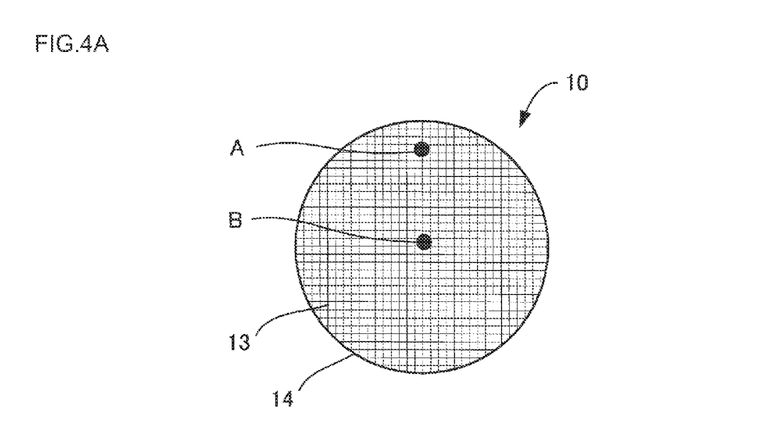
FIG. 4A is an explanatory view showing an end face of a honeycomb structure and showing temperature measurement points of Examples.
Figure 4B:
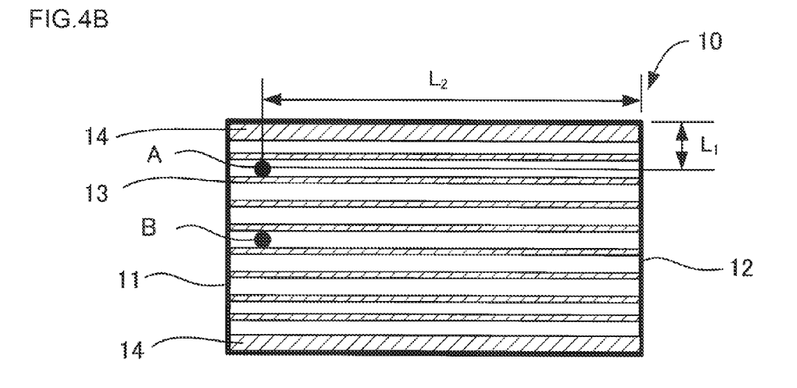
FIG. 4B is an explanatory view showing a section of the honeycomb structure and showing the temperature measurement points of Examples.

The temperature of the first end face 11 during cooling was measured by using a radiation thermometer 9 in real-time, and the internal temperature of the honeycomb structure was measured at two points by a thermocouple 6 provided from a second end face 12 side as shown in FIGS. 4A and 4B. Point A was present at 10 mm downward from the upper end of the honeycomb structure ($L_1$=10 mm) and at 90 mm from the second end face 12 side ($L_2$=90 mm), and point B was present at the center of the face of the honeycomb structure and at 90 mm from the second end face 12 side. Since the longitudinal length of the honeycomb structure was 100 mm, the points A and B were at 10 mm from the first end face 11. On the basis of the temperature measurement results of the first end face 11 and the internal temperature measurement results of the honeycomb structure, temperature differences between the point A and the point B (the temperature gradient of the ceramic body 10) were obtained through a simulation. Thereafter, the occurrence of cracks in the honeycomb structure was checked by using a microscope.

Example 2

The test was performed in the same manner as in Example 1 except that Sample 2 was used.

Comparative Example 1

Sample 1 was heated by using a burner at 1000° C. for 5 minutes, and a cooling gas at 200° C. to 300° C. was ejected for 5 minutes to cool the honeycomb structure. This heating and cooling cycle was repeated 10 times. Temperature measurement during cooling was performed only by providing thermocouples 6 at the point A and the point B of FIGS. 4A and 4B, measuring the internal temperature of the honeycomb structure, and obtaining temperature differences between the point A and the point B (temperature measurement performed by other than the thermocouples was absent). Thereafter, as in Example 1, the absence or presence of the occurrence of cracks in the honeycomb structure was checked.

Comparative Example 2

The test was performed in the same manner as in Comparative Example 1 except that Sample 2 was used.

Comparative Example 3

Sample 1 was mounted in an actual engine bench, and a cycle of heating at 950° C. for 5 minutes and cooling at 200° C. for 5 minutes was repeated 800 times. The test was performed while the other conditions were the same as those of Comparative Example 1.

Comparative Example 4

The test was performed in the same manner as in Comparative Example 3 except that Sample 2 was used.

TABLE 1

| | Thermal shock resistance testing method | Sample | A-B temperature difference (° C.) | | | | | |
|---|---|---|---|---|---|---|---|---|
| | | | 100 | 125 | 150 | 175 | 200 | 225 |
| Example 1 | Electric furnace | 1 | — | Good | Good | Good | Good | Bad |
| Example 2 | Electric furnace | 2 | — | Good | Good | Good | Bad | Bad |
| Comparative Example 1 | Burner | 1 | Good | Good | Good | Good | Bad | — |
| Comparative Example 2 | Burner | 2 | Good | Good | Good | Good | Bad | — |
| Comparative Example 3 | Engine | 1 | Good | Good | Good | Good | Bad | — |
| Comparative Example 4 | Engine | 2 | Good | Good | Good | Bad | Bad | — |

Table 1 shows the temperature gradient of the ceramic body 10, and specifically, whether or not cracks had occurred due to the temperature differences between the point A and the point B. A case where cracks had not occurred was indicated by "Good", and a case where cracks had occurred was indicated by "Bad". Cracks had occurred at 225° C. in Example 1 while cracks had occurred at 200° C. in Example 2. That is, in Examples 1 and 2, since heating was performed in the tubular furnace 2 and cooling was performed by using the cooling gas, the difference in the thermal shock resistance between Sample 1 and Sample 2 could be clearly shown. In addition, since the temperatures were measured by using the radiation thermometer 9 and the thermocouple 6 and the temperature differences (temperature gradient) were calculated through the simulation, the temperature difference between the points A and B was increased (the temperature difference between the points A and B was increased up to 225° C.). That is, it can be considered that in Examples 1 and 2, the temperature gradient of the ceramic body 10 could be obtained with reasonable accuracy.

In the thermal shock resistance testing methods of Comparative Examples 1 and 2 in which the burner was used, the temperature differences of the ceramic bodies 10 due to input gas conditions were less likely to be obtained, and there was no difference in the thermal shock resistance between the samples (in both of Comparative Examples 1 and 2, cracks had not occurred when the temperature difference between the points A and B was 175° C., and cracks had occurred when the temperature difference was 200° C.). In addition, in the thermal shock resistance testing methods of Comparative Examples 3 and 4 in which the engine was used, the difference in the thermal shock resistances between the samples could be checked. However, since the temperatures were measured only by the thermocouple 6, the internal temperature of the ceramic body 10 could not be accurately measured, and the temperature difference between the points A and B was small (the temperature difference between the points A and B was increased only up to 200° C.).

The thermal shock resistance testing method and the thermal shock resistance testing apparatus of the present invention relate to a method and apparatus for testing the thermal shock resistance of various materials while actual use conditions were simulated, and particularly can be used in a thermal shock resistance test of a honeycomb structure such as a three-way catalyst carrier for gasoline vehicles in the automobile field.

DESCRIPTION OF REFERENCE NUMERALS

1: thermal shock resistance testing apparatus, 2: furnace, 3: open end, 3*a*: first open end, 3*b*: second open end, 4:

cooling gas ejecting device, 5: cooling gas ejecting nozzle, 5a: support bar, 5b: heat shielding portion, 6: thermocouple, 7: data logger, 9: radiation thermometer, 10: ceramic body, 11: first end face, 12: second end face, 13: partition wall, 14: circumferential wall, 15: center axis, 20: movement unit, 20a: pedestal, 20b: handle, 21: heater, 22: furnace core tube, 23: shielding portion, 23a: cover (provided in open end), 24: cover (provided in second open end), 24a: slit, 25: mat, 26: fastener, 30: cooling device shutter connection arm, 31: rail, 32: shutter, 33: caster, 34: bar, 35: air cylinder.

What is claimed is:

1. A thennal shock resistance testing method comprising:
   heating a ceramic body in a furnace to a predetermined temperature;
   ejecting a cooling gas toward a first end face of the ceramic body heated in the furnace so that the first end face of the ceramic body is cooled;
   measuring a temperature of the first end face of the ceramic body by using a radiation thermometer provided on the same side from which the cooling gas is ejected, and measuring an internal temperature of the ceramic body by using a thermocouple provided inside the ceramic body;
   thereafter obtaining a temperature gradient of the ceramic body from measurement results of the temperature of the first end face of the ceramic body and the internal temperature of the ceramic body;
   checking an absence or presence of a crack that occurs to the ceramic body; and
   evaluating thermal shock resistance of the ceramic body.

2. The thermal shock resistance testing method according to claim 1,
   wherein, after heating the ceramic body in the furnace, moving the first end face of the ceramic body to an open end of the furnace so that the first end face of the ceramic body is cooled.

3. The thermal shock resistance testing method according to claim 1,
   wherein the ceramic body is disposed in the furnace in a state where a protection material is disposed on an outer circumferential surface of the ceramic body.

4. A thermal shock resistance testing apparatus comprising:
   a furnace which heats a ceramic body;
   a cooling gas ejecting device which ejects a cooling gas for cooling a first end face of the ceramic body from outside of the furnace;
   a radiation thermometer which measures a surface temperature of the first end face; and
   a thermocouple which measures an internal temperature of the ceramic body,
   wherein the first end face of the ceramic body is cooled by the cooling gas, the surface temperature of the first end face of the ceramic body is measured by the radiation thermometer, and the internal temperature of the ceramic body is measured by the thermocouple; and
   wherein the radiation thermometer and the thermocouple are configured to obtain a temperature gradient of the ceramic body from results of the temperature of the first end face of the ceramic body measured by the radiation thermometer and the internal temperature of the ceramic body measured by the thermocouple.

5. The thermal shock resistance testing apparatus according to claim 4,
   wherein a movement unit which moves the ceramic body in the furnace to dispose the first end face of the ceramic body at an open end of the furnace is provided in the furnace, and
   the first end face of the ceramic body is disposed at the open end of the furnace so that the first end face of the ceramic body is cooled by the cooling gas.

6. The thermal shock resistance testing apparatus according to claim 5,
   wherein a furnace core tube is provided in the furnace, and
   the movement unit is a pedestal which has a shape that follows a shape of the furnace core tube, and moves in the furnace core tube.

7. The thermal shock resistance testing apparatus according to claim 5,
   wherein the movement unit includes a fixing unit which fixes the thermocouple.

8. The thermal shock resistance testing apparatus according to claim 4,
   wherein a shutter as a shielding portion which shields heat is provided at an open end of the furnace on a side where the first end face of the ceramic body is disposed.

9. The thermal shock resistance testing apparatus according to claim 4,
   wherein the radiation thermometer is installed in a direction at 10° to 60° from a direction perpendicular to the first end face of the ceramic body.

* * * * *